Figure 1:
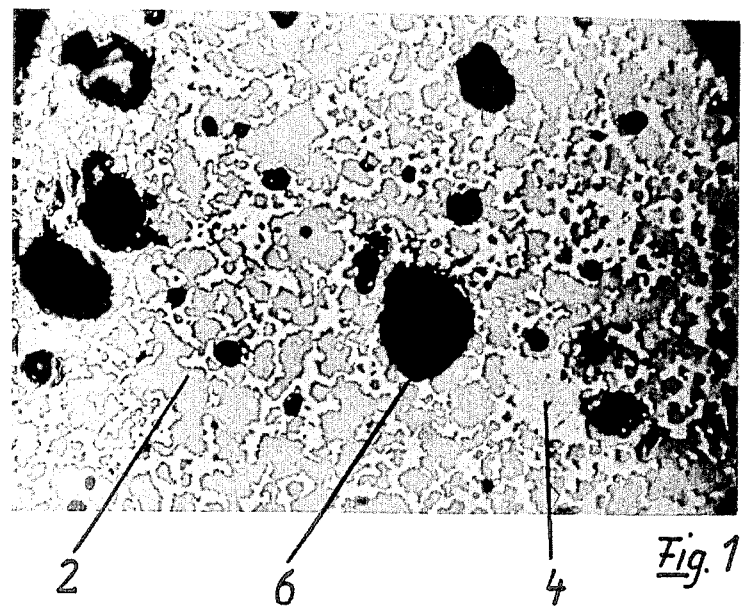

United States Patent [19]

Schmidberger et al.

[11] 4,197,362
[45] Apr. 8, 1980

[54] INTERCONNECTOR MATERIAL FOR SERIES-CONNECTED ELECTROLYTIC CELLS OPERATED AT HIGH TEMPERATURES

[75] Inventors: Rainer Schmidberger, Bermatingen; Wolfgang Donitz, Immenstaad, both of Fed. Rep. of Germany

[73] Assignee: Dornier System GmbH, Friedrichshafen, Fed. Rep. of Germany

[21] Appl. No.: 928,170

[22] Filed: Jul. 26, 1978

[30] Foreign Application Priority Data

Aug. 10, 1977 [DE] Fed. Rep. of Germany ....... 2735934

[51] Int. Cl.² ............................................. H01M 8/00
[52] U.S. Cl. ...................................... 429/12; 252/521; 427/115; 428/539; 429/224
[58] Field of Search ....:......................... 429/12, 27–29, 429/40–45, 160, 224; 252/462, 521, 62.3; 427/115; 428/538, 539

[56] References Cited

U.S. PATENT DOCUMENTS

| 3,644,147 | 2/1972 | Young | 429/40 |
|---|---|---|---|
| 3,861,961 | 1/1975 | Kudo et al. | 429/42 |
| 3,922,204 | 11/1975 | Tseung et al. | 252/462 X |
| 4,133,778 | 1/1979 | Gray | 252/521 X |

*Primary Examiner*—Charles F. LeFevour
*Attorney, Agent, or Firm*—Toren, McGeady and Stanger

[57] ABSTRACT

A body suitable for conductively connecting respective electrodes of closely coupled fuel cells arranged in series circuit and operating at temperatures of at least 600° C. consists of two conductively bonded ceramic materials having electronic conductivities of at least one mho/cm at 1000° C. at respective ambient partial oxygen pressures between $10^{-5}$ bar and one bar, and below $10^{-5}$ bar.

2 Claims, 2 Drawing Figures

INTERCONNECTOR MATERIAL FOR SERIES-CONNECTED ELECTROLYTIC CELLS OPERATED AT HIGH TEMPERATURES

This invention relates to high-temperature fuel cells and similar electrolytic apparatus operating at temperatures of at least 600° C. and typically 1000° C., and particularly to a material suitable for conductively connecting respective electrodes of closely coupled, series-connected cells of such apparatus.

Because of the stresses imposed on the inter-connector material, it should satisfy simultaneously the following requirements:

(1) It should have an electronic conductivity of at least 1 mho/cm at about 1000° C. to minimize electrical losses.

(2) It should maintain such high conductivity at high temperature at the very different, ambient, partial oxygen pressures prevailing near the two connected electrodes which may be of the order of 1 bar at one electrode and of $10^{-16}$ bar at the other electrode.

(3) Its ionic conductivity should preferably be low.

(4) It should be mechanically and chemically stable over the entire encountered range of partial oxygen pressures.

(5) It must be capable of being shaped into layers or other bodies practically impermeable to gases.

(6) Its coefficient of thermal expansion should be close to that of the connected electrodes and electrolyte.

(7) The properties enumerated above should not be altered by extended contact with other materials of the electrolytic apparatus under the operating conditions indicated.

The only materials known heretofore and satisfying the several conditions outlined above in an acceptable manner are noble metals, such as gold, platinum, and their alloys whose high cost militates against their application.

Various conductive oxides have been proposed as substitute materials at lower cost, but the cost advantage is offset by significantly impaired performance. C. C. Sun et al. [J. Electrochem. Soc. 119 (11) 1433] have proposed the use of $CoCr_2O_4$. However, this material has quite low conductivity and its coefficient of thermal expansion is very different from that of zirconium oxide, a structural material commonly employed in high-temperature electrolytic cells.

T. L. Markin et al. ("Superionic conductors", G. D. Mahan et al., ed., Plenum Press, New York, p. 26) have recommended the use of niobium-doped titanium dioxide. However, conductivity of this material is low in oxidizing atmospheres. W. Baukal et al [J. Power Sources 1 (1976/7) 203] and R. J. Ruka (Extended Abstracts of Workshop on "High Temperature Solid Oxide Fuel Cells", May 5-6, 1977, Brookhaven National Laboratory) have disclosed the use of lanthanum chromites doped with Mg, Sr, Al, Co, Ni. However, these materials cannot be sintered to make them gastight at available temperatures, and their electrical conductivity at 1000° C. and ambient partial oxygen pressure of $10^{-16}$ bar is well below 1 mho/cm.

Lanthanum manganites containing strontium have been disclosed as connector material in French Pat. No. 2,099,542. They have very high conductivity in oxidizing atmospheres, but their perofskite structures decompose at 1000° C. at partial oxygen pressures of less than $10^{-15}$ bar.

The primary object of this invention is the provision of a body of ceramic material which is electrically conductive and practically impermeable to gases, avoids the technical shortcomings of the afore-described oxide materials and the high cost of the noble metals, and satisfies the seven criteria to an acceptable extent.

It has been found that some of the known ceramic oxides enumerated above which are unsatisfactory when used individually as inter-connector materials, perform very well if combined with each other by conductive bonding. The invention provides, as an inter connector for high-temperature electrolytic cells, such as fuel cells, a body consisting essentially of a first ceramic material whose electronic conductivity is at least one mho/cm at all ambient partial oxygen pressures between $10^{-5}$ bar and one bar at 1000° C., and a second ceramic material whose electronic conductivity at all ambient partial oxygen pressures lower than $10^{-5}$ bar and at 1000° C. is at least 1 mho/cm. The two materials are conductively bonded to each other as by sintering mixtures of their intimately mixed powders, by diffusion welding, or by means of adhesives or solders.

Mixed oxides of the formula $LaMnO_3$ in which La may be replaced in part by Ca, Sr, or Ba and which have perofskite structure have the required high electronic conductivity in an oxidizing atmosphere, that is, an atmosphere in which the partial oxygen pressure is above $10^{-5}$ bar. High conductivity in reducing atmospheres is possessed by the so-called reduction semiconductors $TiO_2$ and $CeO_2$, and may be improved greatly by doping agents.

Highest electronic conductivity under both oxidizing and reducing conditions and at high temperature has been achieved so far with inter connector bodies in which the two components form respective coherent networks which are interengaged with each other.

Figure 2:
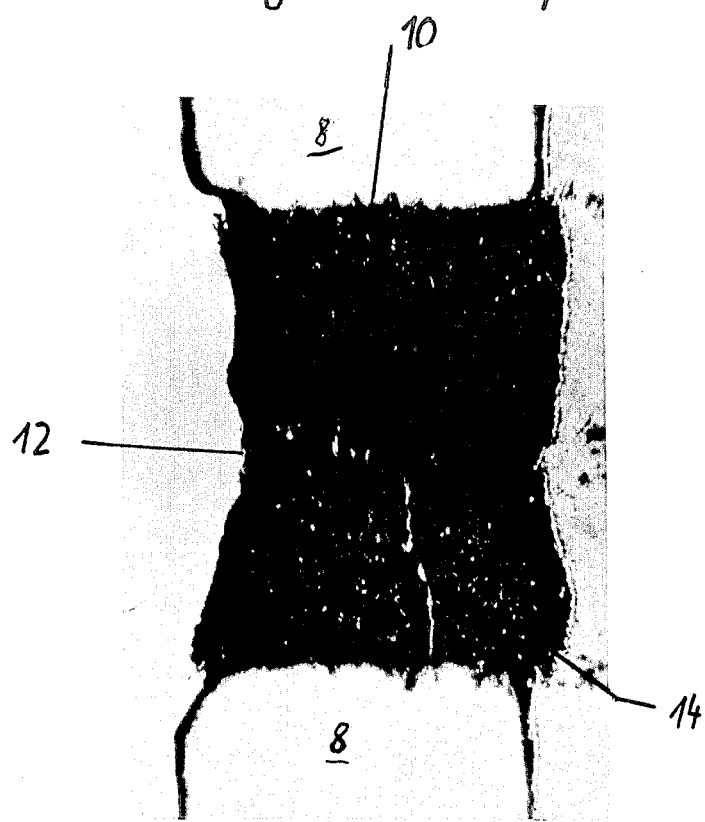

Representative compound bodies of the invention are illustrated in the attached drawing in which:

FIG. 1 is an actual photomicrograph of a first embodiment of the invention taken at 700× magnification; and FIG. 2 is an actual photomicrograph of a second embodiment taken at 70× magnification.

The material illustrated in FIG. 1 consists essentially of two ceramic phases 2, 4 constituting two, three-dimensional, continuous, but densely interengaged or interlocked networks in which a few small, closed pores 6 are dispersed without impairing the substantial impermeability of the material to gases.

The material shown in FIG. 1 was prepared by intimately mixing equal volumes of powders of $La_{0.5}Ca_{0.5}MnO_3$ and $(CeO_2)_{0.995}(V_2O_5)_{0.005}$ having grains smaller than $20\mu$, compressing the powder mixture, and sintering the green compact in air for four hours at 1400° C.

FIG. 2 shows a laminar material of the invention as a dark zone between two bodies 8 of electrolyte grade zirconia which appears light. The material of the invention consists of a core layer 12 of $TiO_2$ doped with 10 mole percent $Nb_2O_5$ and two layers 10, 14 welded to opposite faces of the core layer by thermal diffusion and consisting of $La_{0.8}Ba_{0.2}MnO_3$ having perofskite structure. The three layers were prepared separately by compacting respective powders and sintering the compacts. They were then compressed between the zirconia bodies and the assembly heated at high pressure applied to the $ZrO_2$ bodies until the three layers 10, 12, 14 diffused into each other to the extent shown in the micrograph.

Conductivities at 1000° C. of the materials referred to in the description of FIGS. 1 and 2 and of others, also representative of this invention, that may be substituted therefor are listed below.

| Materials of high conductivity in oxidizing atmosphere | |
|---|---|
| ($p_{O_2}$ = 0.21 bar) | |
| $La_{0.5}Ca_{0.5}MnO_3$ | 130 mho/cm |
| $La_{0.8}Ba_{0.2}MnO_3$ | 100 mho/cm |
| $La_{0.8}Ba_{0.2}Cr_{0.2}Mn_{0.8}O_3$ | 25 mho/cm |
| $La_{0.5}Sr_{0.5}MnO_3$ | 100 mho/cm |

| Materials of high conductivity in reducing atmospheres | |
|---|---|
| ($p_{O_2}$ = $10^{-15}$ bar) | |
| $(CeO_2)_{0.995}(V_2O_5)_{0.005}$ | 7 mho/cm |
| $(CeO_2)_{0.995}(Nb_2O_5)_{0.005}$ | 4 mho/cm |
| $(TiO_2)_{0.9}(Nb_2O_5)_{0.1}$ | 53 mho/cm |
| $(CeO_2)_{0.995}(Ta_2O_5)_{0.005}$ | 1.5 mho/cm |
| $(CeO_2)_{0.95}(Ta_2O_5)_{0.05}$ | 45 mho |

The compound materials of the invention have been used successfully in high-temperature fuel cells for interconnecting oxygen and fuel electrodes of two cells, but also with air and steam electrodes. They also perform well as electrodes operating under conditions of widely varying partial oxygen pressure as in oxygen probes and waste gas sensors. Electrodes prepared from the materials of the invention are characterized by substantially constant conductivity in atmospheres whose composition varies.

The presently preferred ceramic materials listed above may be modified in an obvious manner. In the materials having high electronic conductivity in oxidizing atmospheres, the presence of doping additions is not absolutely necessary, and pure $LaMnO_3$ has adequate conductivity. The alkaline earth metal oxides employed as doping agents should not replace substantially more than 50 mole percent of the lanthanum oxide. The oxides of Ca, Ba, Sr are practically interchangeable. Not more than 50 mole percent of the manganese oxide moiety may be replaced by chromium oxide, and manganese should predominate.

The electronic conductivity of the materials having high conductivity in reducing atmospheres is more sensitive to the quantity of doping agents, but the effects of $V_2O_5$, $Nb_2O_5$, and $Ta_2O_5$ on $CeO_2$ and $TiO_2$ in equal quantities are of a similar order of magnitude, $TiO_2$ and $CeO_2$ being roughly equivalent.

The several materials having high conductivity in oxidizing atmospheres may be combined with any one of the materials having high conductivity in reducing atmospheres. No advantages have been observed yet in compound materials including more than one component suitable for oxidizing atmosphere with one or more than one component suitable for reducing atmospheres, and binary compound bodies are preferred at this time because of their more convenient preparation.

It should be understood, therefore, that the foregoing disclosure relates only to presently preferred embodiments, and that it is intended to cover all changes and modifications of the examples of the invention herein chosen for the purpose of the disclosure which do not constitute departures from the spirit and scope of the invention set forth in the appended claims.

What is claimed is:

1. An electrically conductive body substantially impervious to gases and chemically and mechanically stable at a temperature of 1000° C., said body consisting essentially of at least one first ceramic material having an electronic conductivity of at least one mho/cm at all ambient partial oxygen pressures between $10^{-5}$ bar and one bar at said temperature, and at least one second ceramic material having an electronic conductivity of at least one mho/cm at all ambient partial oxygen pressures lower than $10^{-5}$ bar at said temperature, said materials being conductively bonded to each other wherein said at least one first material is a mixed oxide of the formula $LaMnO_3$ having perofskite structure, and said at least one second material is $CeO_2$ or $TiO_2$ doped with 0.1 to 10 mole percent of an oxide selected from the group consisting of $Nb_2O_5$, $V_2O_5$, and $Ta_2O_5$.

2. An electrically conductive body substantially impervious to gases and chemically and mechanically stable at a temperature of 1000° C., said body consisting essentially of at least one first ceramic material having an electronic conductivity of at least one mho/cm at all ambient partial oxygen pressures lower than $10^{-5}$ bar and one bar at said temperature, and at least one second ceramic material having an electronic conductivity of at least one mho/cm at all ambient partial oxygen pressures lower than $10^{-5}$ bar at said temperature, said materials being conductively bonded to each other wherein said at least one first material is a mixed oxide of the formula $XYO_3$, wherein X includes La, the balance of said X, not substantially exceeding 50 mole percent, consisting essentially of Ca, Sr, or Ba, and Y consists predominantly of Mn, the balance of said Y consisting essentially of Cr, said mixed oxide having perofskite structure, and said at least one second material is $CeO_2$ or $TiO_2$ doped with 0.1 to 10 mole percent of an oxide selected from the group consisting of $Nb_2O_5$, $V_2O_5$ and $Ta_2O_5$.

* * * * *